(12) United States Patent
Prudnikov et al.

(10) Patent No.: US 8,348,965 B2
(45) Date of Patent: Jan. 8, 2013

(54) ROTATIONAL ATHERECTOMY DEVICE WITH COUNTERWEIGHTING

(75) Inventors: Dmitriy Prudnikov, Moscow (RU); Larry A. Walter, Minneapolis, MN (US); Jeffrey A. McBroom, Champlin, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 0 days.

(21) Appl. No.: 11/876,891

(22) Filed: Oct. 23, 2007

(65) Prior Publication Data

US 2009/0105736 A1 Apr. 23, 2009

(51) Int. Cl.
*A61B 17/22* (2006.01)

(52) U.S. Cl. ...................................... 606/159

(58) Field of Classification Search ............. 606/108, 606/159, 170, 180, 194, 200; 604/264
See application file for complete search history.

(56) References Cited

U.S. PATENT DOCUMENTS

| | | | | |
|---|---|---|---|---|
| 1,431,416 | A | * | 10/1922 | Parsons et al. .................. 74/597 |
| 4,779,316 | A | * | 10/1988 | Cherry et al. .................... 74/603 |
| 5,312,427 | A | | 5/1994 | Shturman |
| 5,554,163 | A | | 9/1996 | Shturman |
| 6,132,444 | A | * | 10/2000 | Shturman et al. ............. 606/159 |
| 6,146,395 | A | | 11/2000 | Kanz et al. |
| 6,217,595 | B1 | | 4/2001 | Shturman et al. |

| | | |
|---|---|---|
| 2009/0018564 A1 | 1/2009 | Shturman |
| 2009/0069829 A1 | 3/2009 | Shturman |
| 2009/0182359 A1 | 7/2009 | Shturman |

FOREIGN PATENT DOCUMENTS

| | | | |
|---|---|---|---|
| GB | 2426458 A | * | 11/2006 |
| JP | 8-509390 | | 10/1996 |
| WO | 2006/126076 | | 11/2006 |
| WO | 2006/126175 | | 11/2006 |
| WO | 2006/126176 | | 11/2006 |
| WO | WO2006/126176 | | 11/2006 |
| WO | 2008/006705 | | 1/2008 |
| WO | 2008/006706 | | 1/2008 |
| WO | 2008/006708 | | 1/2008 |
| WO | 20081006704 | | 1/2008 |
| WO | 2008/062069 | | 5/2008 |

* cited by examiner

*Primary Examiner* — Ryan Severson
*Assistant Examiner* — Ashley Cronin
(74) *Attorney, Agent, or Firm* — Winthrop & Weinstine, P.A.

(57) ABSTRACT

The invention provides a rotational atherectomy device having a flexible, elongated, rotatable drive shaft with an abrasive section comprising an enlarged diameter section of the drive shaft or, alternatively, a solid abrasive crown which may be attached to the drive shaft. The device further comprises a proximal and/or a distal counterweight attached to the drive shaft, spaced from the abrasive section wherein each counterweight has its center of mass offset from the longitudinal axis of the drive shaft to stimulate orbital motion by the abrasive section. When placed within an artery against stenotic tissue and rotated at sufficiently high speeds (e.g., in the range of about 20,000 rpm to about 200,000 rpm) the orbiting nature of the abrasive section causes such section to rotate as to open the stenotic lesion to a diameter substantially larger than the resting outer diameter of the abrasive section.

6 Claims, 9 Drawing Sheets

PRIOR ART

ROTATIONAL ATHERECTOMY DEVICE WITH COUNTERWEIGHTING

BACKGROUND OF THE INVENTION

1. Field of the Invention

The invention relates to devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a concentrically shaped ellipsoidal burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently, since the burr is of a fixed resting diameter, more than one size burr must be utilized to open an artery to the desired diameter. No other variables are disclosed by the Auth device that would allow sweeping a variable diameter, or a diameter larger than the burr's resting diameter, during high-speed rotation.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., rotational speeds within the range of about 20,000-200,000 rpm. Essentially, the center of mass offset from the rotational axis of the drive shaft would result in development of significant and undesirable centrifugal force, exerting too much pressure on the wall of the artery and creating too much heat and excessively large particles. As with Auth, the burr size is fixed and may require using more than one size burr to open the subject lumen to the desired diameter.

U.S. Pat. Nos. 6,132,444 (Shturman) and 6,494,890 (Shturman) disclose, inter alia, an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The orbital rotational motion is primarily due to the offset of the center of mass of the enlarged eccentric section from the drive shaft's rotational axis. Since the enlarged eccentric section may comprise drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. The disclosure of U.S. Pat. Nos. 6,132,444 and 6,494,890 are each hereby incorporated by reference in their entirety.

BRIEF SUMMARY OF THE INVENTION

The invention provides a rotational atherectomy device having a flexible, elongated, rotatable drive shaft with an abrasive section comprising an enlarged diameter section of the drive shaft or, alternatively, a solid abrasive crown which may be attached to the drive shaft. The device further comprises a proximal and/or a distal counterweight attached to the drive shaft, spaced from the abrasive section wherein each counterweight has its center of mass offset from the longitudinal axis of the drive shaft to stimulate orbital motion by the abrasive section. When placed within an artery against stenotic tissue and rotated at sufficiently high speeds (e.g., in the range of about 20,000 rpm to about 200,000 rpm) the orbiting nature of the abrasive section causes such section to rotate as to open the stenotic lesion to a diameter substantially larger than the resting outer diameter of the abrasive section.

An object of the invention is to provide a high-speed rotational atherectomy device having an abrasive section with a high-speed rotational diameter that is greater than its resting diameter.

An object of the invention to provide a high-speed rotational atherectomy device having a concentric abrasive section with a high-speed rotational diameter that is greater than its resting diameter.

Another object of the invention is to provide a high-speed rotational atherectomy device having an eccentric abrasive section with a high-speed rotational diameter that is greater than its resting diameter.

Another object of the invention is to provide a high-speed rotational atherectomy device having two counterweights on the drive shaft, one located proximally and one located distally to the abrasive section.

Another object of the invention is to provide a high-speed rotational atherectomy device having at least one counterweight on the drive shaft, the at least one counterweight located either proximally or distally to the abrasive section.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
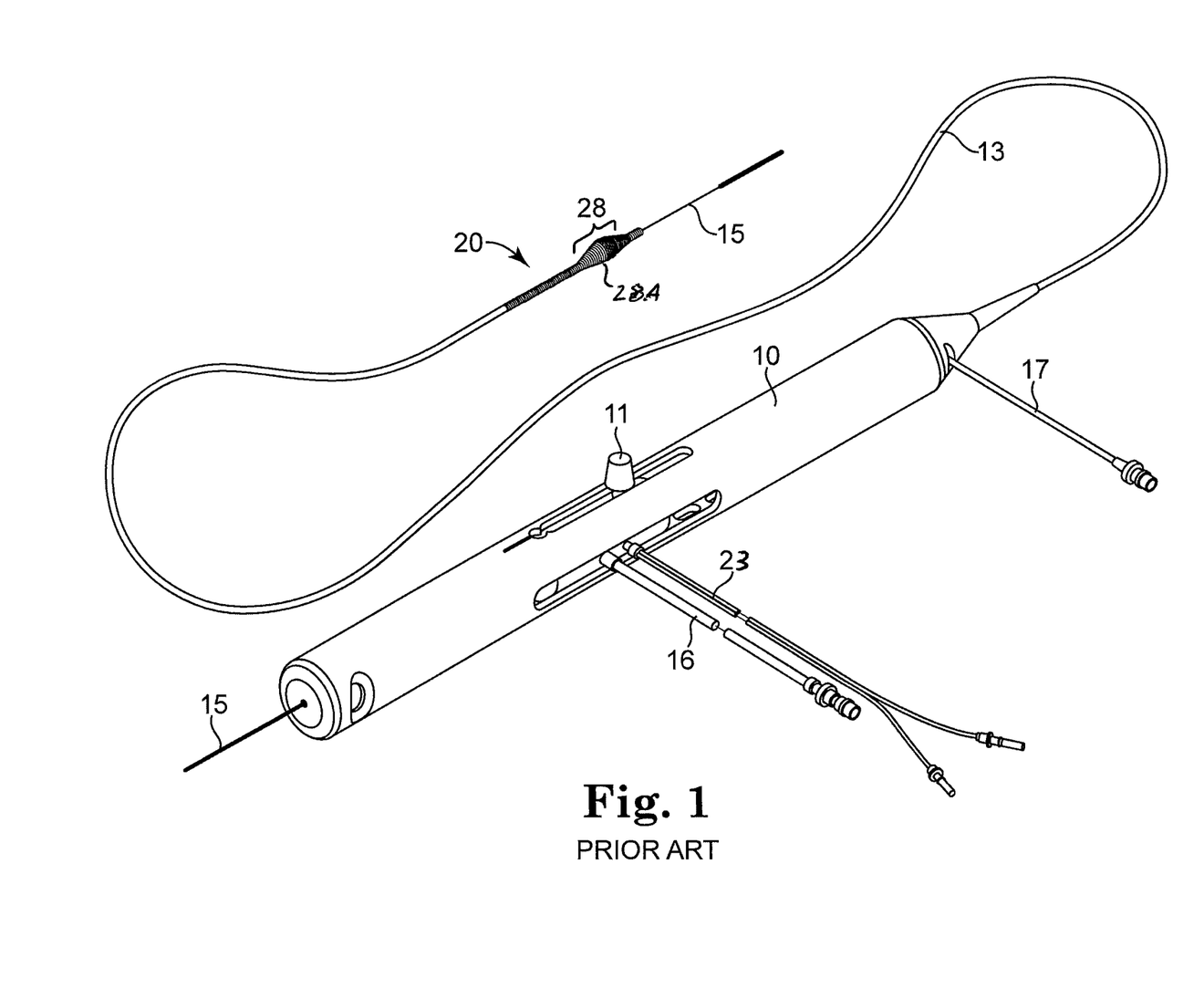
FIG. 1 is a perspective view of one embodiment of a non-flexible eccentric cutting head of a rotational atherectomy device of the invention.

FIG. 1 illustrates a typical rotational atherectomy device of the invention. The device includes a handle portion 10, an elongated, flexible drive shaft 20 having an abrasive section 28 comprising an eccentric enlarged diameter section 28A, and an elongated catheter 13 extending distally from the handle portion 10. The drive shaft 20 and its eccentric enlarged diameter section 28 are constructed from helically coiled wire. The catheter 13 has a lumen in which most of the length of the drive shaft 20 is disposed, except for the enlarged diameter section 28A and a short section distal to the enlarged diameter section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 23 may also be provided for monitoring the speed of rotation of the turbine and drive shaft 20 (details regarding such handles and associated instrumentation are well know in the industry, and are described, e.g., in U.S. Pat. No. 5,314,407, issued to Auth). The handle 10 also desirably includes a control knob 11 for advancing and retracting the turbine and drive shaft 20 with respect to the catheter 13 and the body of the handle.

Figure 2:
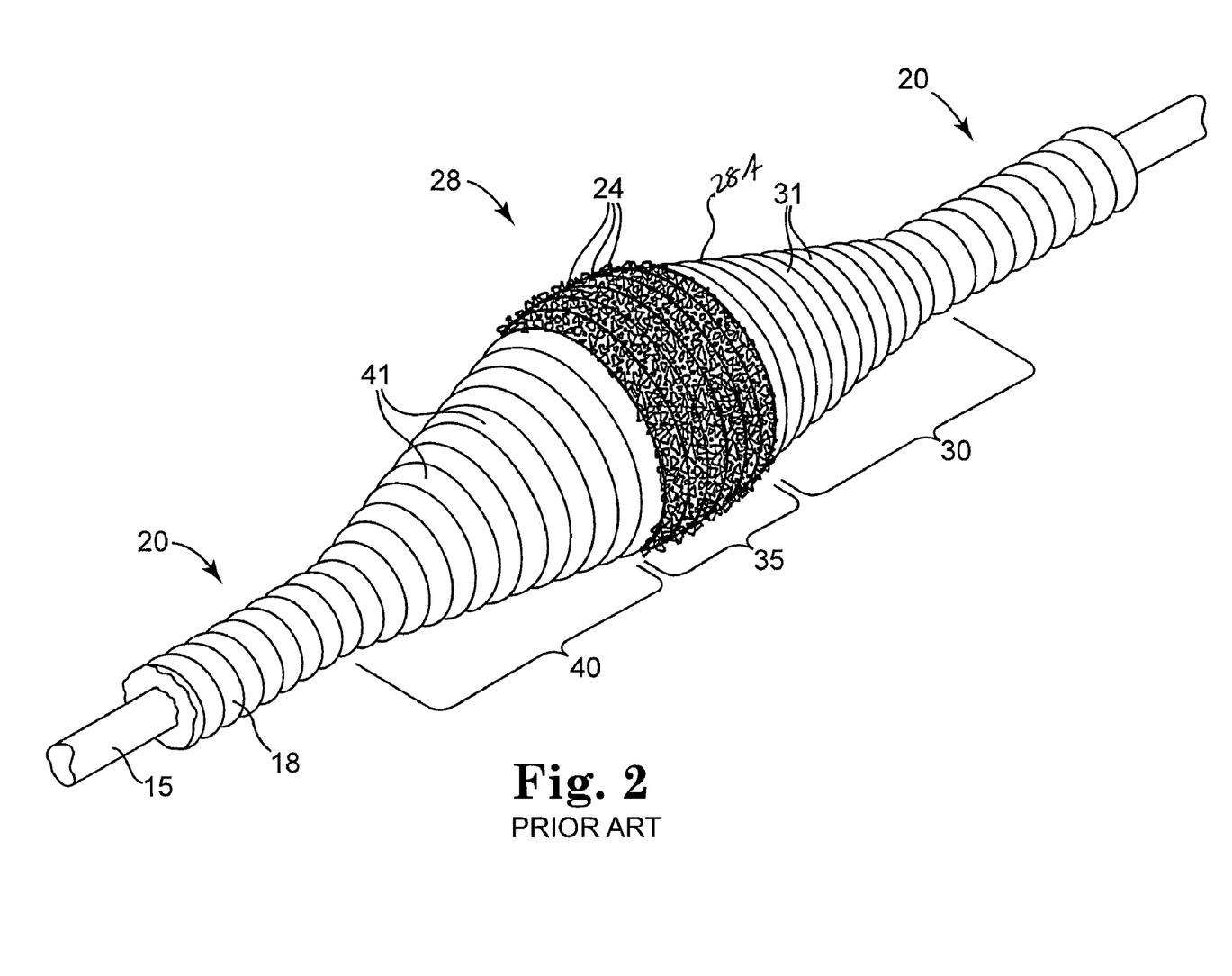
FIG. 2 is perspective, broken-away view of a prior art flexible eccentric enlarged section of the drive shaft.
Figure 3:
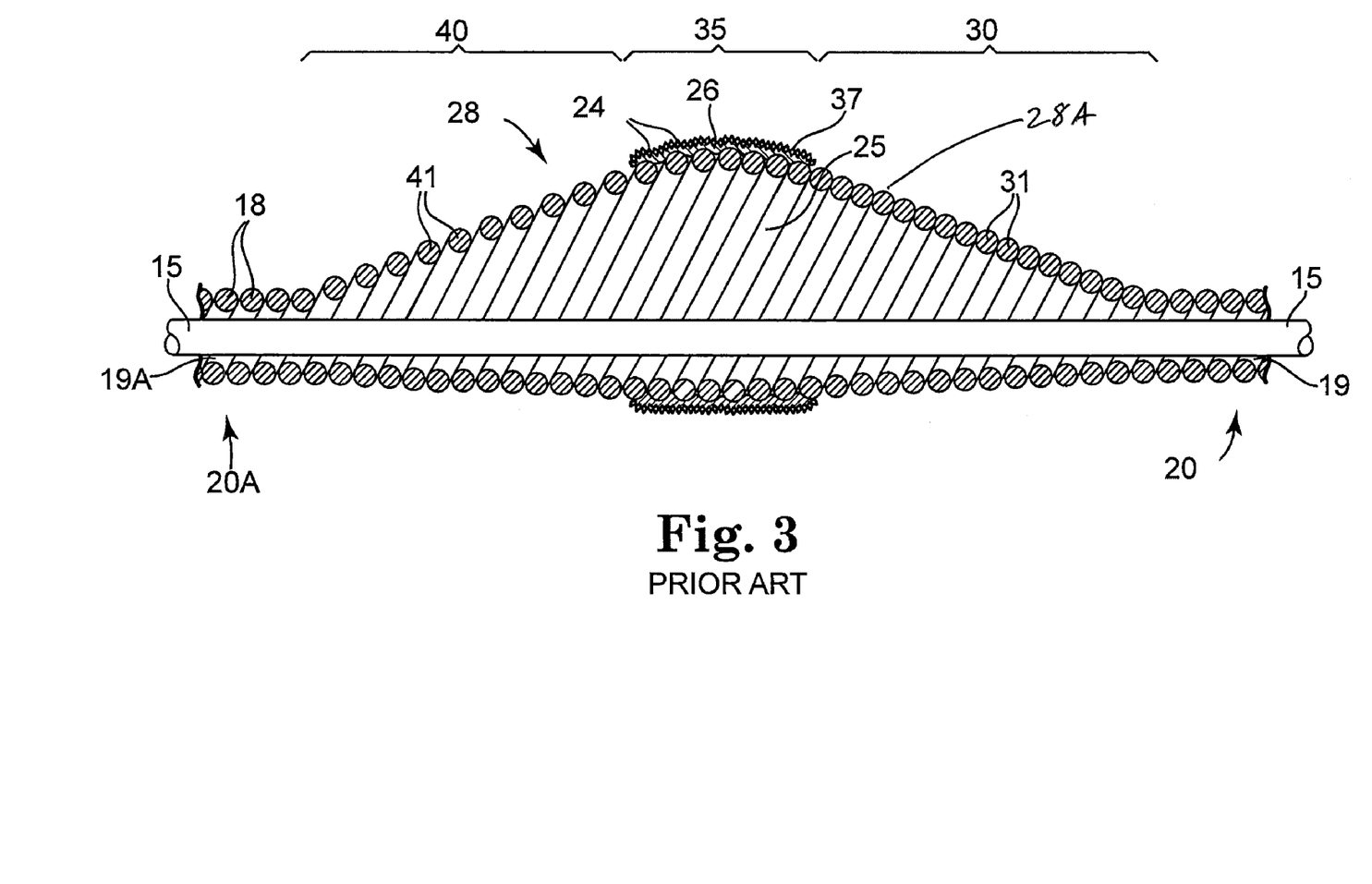
FIG. 3 is a broken-away, longitudinal cross-sectional view of a prior art eccentric enlarged section of the drive shaft.

FIGS. 2-3 illustrate details of abrasive section 28 comprising eccentric enlarged diameter section 28A. The drive shaft 20 is comprised of one or more helically wound wires 18 which define a guide wire lumen 19 and a hollow cavity 25 within the enlarged diameter section 28A. Except for the guide wire 15 traversing the hollow cavity 25, the hollow cavity 25 is substantially empty. Abrasive section 28 illustrated as eccentric enlarged diameter section 28A comprises proximal 30, intermediate 35 and distal 40 portions with a tissue removing surface 37 thereon. Wire turns 31 of the proximal portion 30 of the eccentric enlarged diameter section 28A preferably have diameters that progressively increase distally at a generally constant rate, thereby forming generally the shape of a cone. Wire turns 41 of the distal portion 40 preferably have diameters that progressively decrease distally at a generally constant rate, thereby forming generally the shape of a cone. Wire turns 36 of the intermediate portion 35 are provided with gradually changing diameters to provide a generally convex outer surface which is shaped to provide a smooth transition between the proximal and distal conical portions of the enlarged diameter section 28A of the drive shaft 20.

At least part of the abrasive section 28, illustrated as eccentric enlarged diameter section 28A (preferably the intermediate portion 35) comprises an external surface 37 capable of removing tissue. Preferably the tissue removing surface comprises a coating 37 of an abrasive material 24 to define a tissue removing segment of the drive shaft 20. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the wire turns of the drive shaft 20 by a suitable binder 26—such attachment may be achieved using well known techniques, such as conventional electroplating or fusion technologies (see, e.g., U.S. Pat. No. 4,018,576). Alternately the external tissue removing surface may be simply a section of the wire turns which has been roughened to provide a suitable abrasive surface. In yet another variation, the external surface may be etched or cut (e.g., with a laser) to provide small but sharp cutting surfaces.

Other similar techniques may also be utilized to provide a suitable tissue removing surface.

Figure 4:
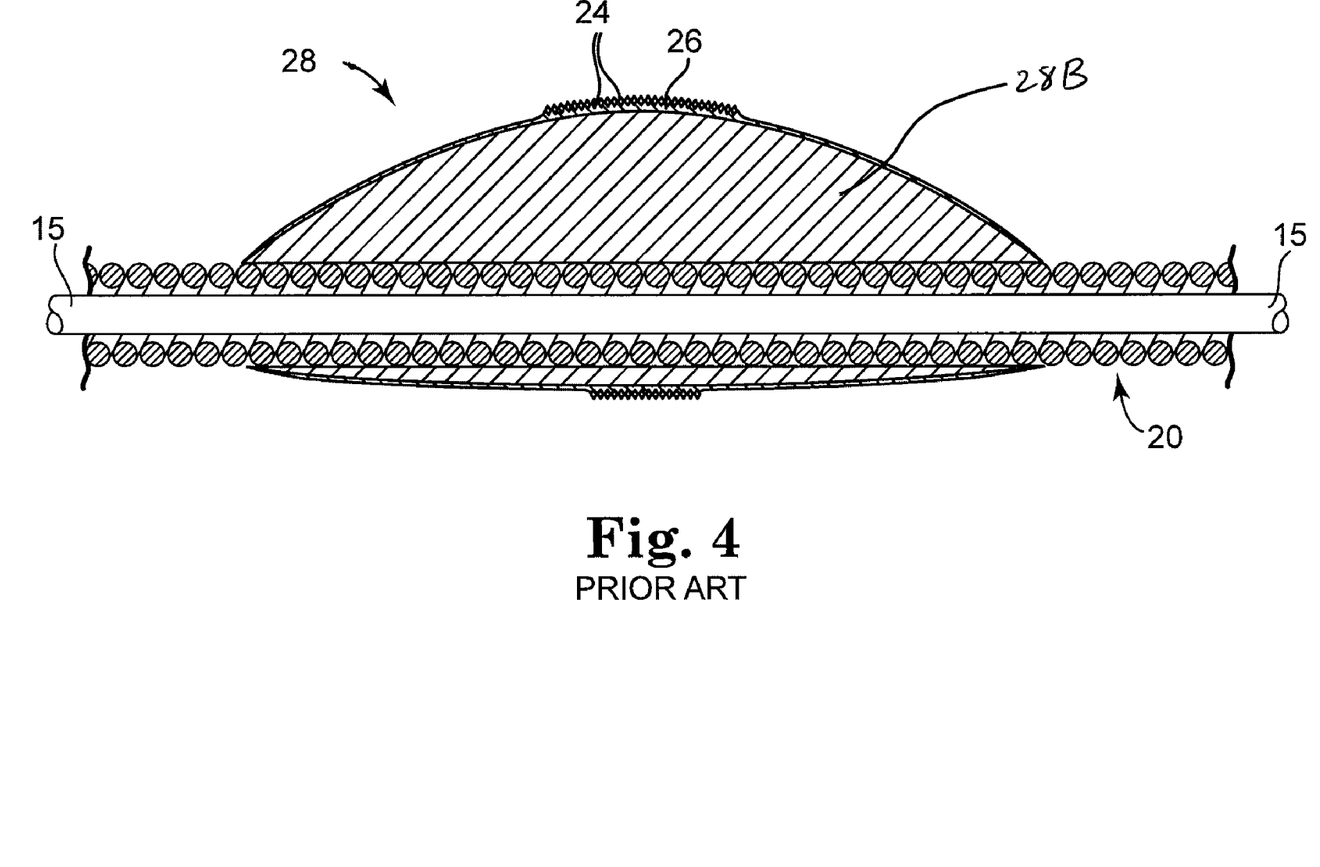
FIG. 4 is a broken-away, longitudinal cross-sectional view illustrating the flexibility of a prior art solid eccentric enlarged burr attached to the drive shaft.

FIG. 4 illustrates another type of known abrasive section 28, illustrated as an eccentric solid, or at least partially hollow, burr 28B. Solid, or at least partially hollow, abrasive burr 28B is attached to drive shaft 20 by means well known in the art and comprises a coating of an abrasive material 24 fixed to the surface by a suitable binder 26.

Figure 5A:
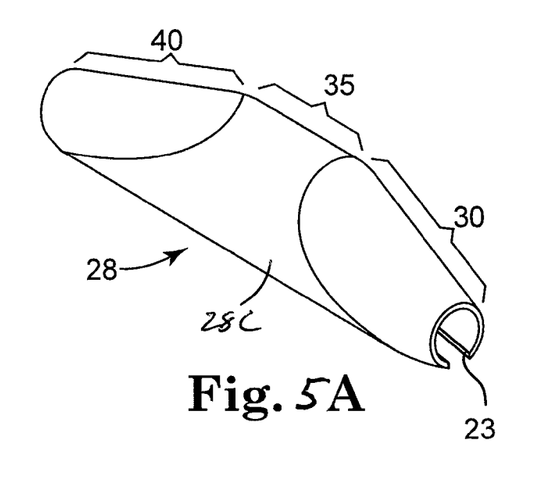
FIG. 5A is a perspective view of a prior art eccentric abrading head or crown that attaches to the drive shaft.
Figure 5B:
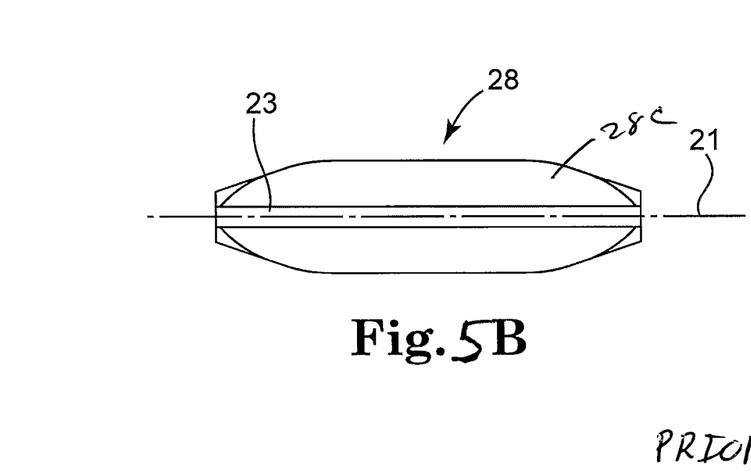
FIG. 5B is a bottom view of a prior art eccentric abrading head or crown that attaches to the drive shaft
Figure 5C:
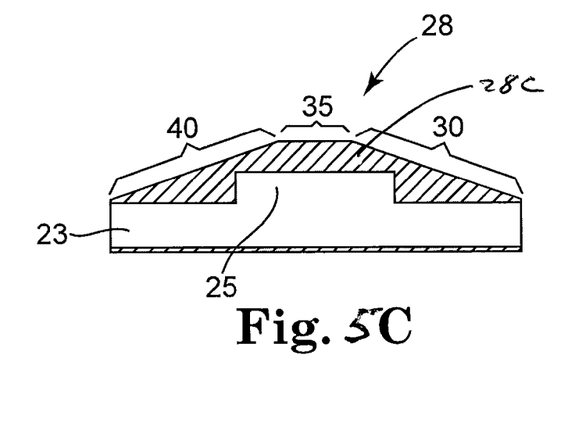
FIG. 5C is a longitudinal cross-section view of a prior art eccentric abrading head or crown that attaches to the drive shaft.

FIGS. 5A, 5B, and 5C illustrate another known abrasive surface 28, comprising an eccentric abrading head or crown 28C as described in U.S. application Ser. No. 11/761,128 to Thatcher et al., the disclosure of which is hereby incorporated by reference in its entirety. Lumen 23 is provided for crimping attachment to the drive shaft 20 and may comprise hollowed section 25 to assist in moving the center of mass either away from, or closer to, the drive shaft 20 axis of rotation. Abrasive section 28C comprises proximal 30, intermediate 35 and distal 40 portions, the proximal 30 and distal 40 portions sloping away from intermediate portion 35, represented as having a cylindrical shape.

Thus, one embodiment according to the present invention comprises an abrasive section 28 that may, in turn, comprise an eccentric enlarged section 28A of the drive shaft, or an eccentric solid crown or abrading head 28C or eccentric burr 28B attached to the drive shaft, wherein the abrasive section 28 has a center of mass spaced radially from the rotational axis of the drive shaft 20, facilitating the ability of the device to open the stenotic lesion to a diameter substantially larger than the outer diameter of the abrasive section 28. This may be achieved by spacing the geometric center of the abrasive section 28, i.e., the eccentric enlarged diameter section of the drive shaft 20, or the eccentric solid abrading head or crown 28C, or burr 28B attached to the drive shaft 20, away from the rotational axis of the drive shaft 20. Alternatively, the center of mass of the abrasive section 28 may be radially spaced from the drive shaft's rotational axis by providing an abrasive section 28 that comprises a differential combination of materials, wherein one side of at least one of the abrasive section 28 comprises a more massive or denser material than the other side, which creates eccentricity as defined herein. As those skilled in the art will recognize, creation of eccentricity by differential use of materials within the structure of the abrasive section 28, e.g., a center of mass offset from the drive shaft's rotational axis, is applicable to any embodiment of the abrasive section 28 discussed herein, whether concentric, eccentric, solid burr, partially hollow crown or abrading head or an enlarged section of the drive shaft, or the equivalent.

Further this particular embodiment of the present invention may comprise at least one counterweight located on, and fixedly attached to, the drive shaft to stimulate orbital motion of the eccentric abrasive section. One such at least one counterweight may be located proximal to the abrasive section, while another at least one counterweight may be located distal to the abrasive section.

Figure 6:
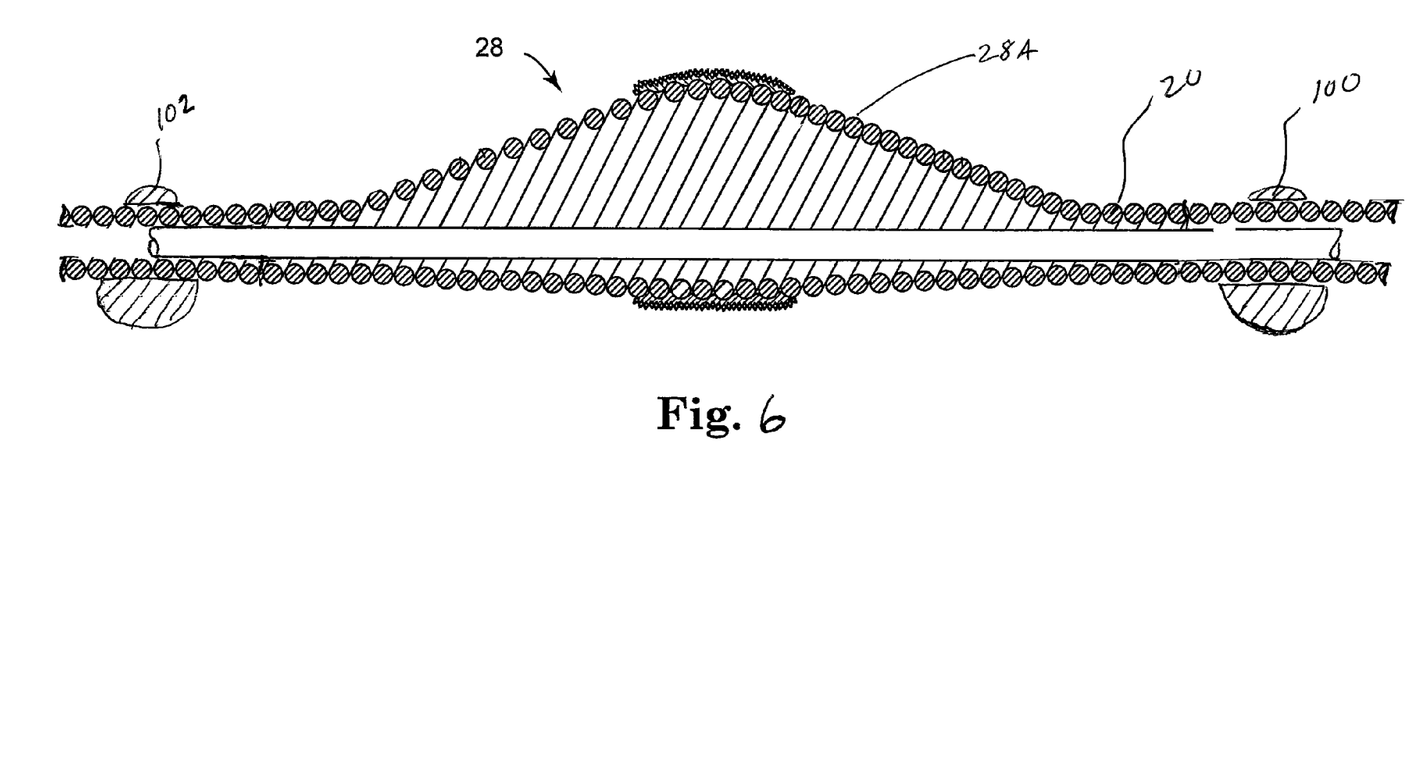
FIG. 6 is a longitudinal cross-section view of one embodiment of the present invention.

In one embodiment, as illustrated in FIG. 6, the abrasive section 28 is represented as eccentric enlarged diameter section 28A of the drive shaft 20. A distal counterweight 100 is located distally of the abrasive section 28 and a proximal counterweight 102 is located proximal to the abrasive section. Alternate embodiments may comprise only the distal counterweight 100 in operative combination with the abrasive section 28 or only the proximal counterweight 102 in operative combination with the abrasive section 28.

As illustrated in FIG. 6, the counterweights 100, 102 are solid and eccentric burrs, though a number of alternative embodiments are contemplated by the present invention.

For example, one or both of the proximal and distal counterweights 100, 102 may comprise enlarged diameter sections of the drive shaft, formed in similar fashion as the enlarged eccentric diameter abrasive section 28A. In this embodiment, the counterweights 100, 102 are essentially hollow, enlarged wire turns of the drive shaft 20, formed by use of a mandrel during the wire turn winding process. In the case where only one, either the proximal 102 or the distal 100, counterweight is an enlarged eccentric diameter abrasive section of the drive shaft 20, the remaining counterweight may be either concentric, i.e., center of mass collinear with the drive shaft's axis of rotation and comprising an enlarged diameter section of the drive shaft, a solid crown or at least partially hollow crown, or may be eccentric and comprising a solid burr or an at least partially hollow crown or abrading head.

Alternatively, one or both of the proximal and distal counterweights 100, 102 may be solid, as illustrated in FIG. 6 and attached to the wire turns of the drive shaft 20 by means well known to those skilled in the art. More alternatively, the proximal and distal counterweights 100, 102 may be at least partially hollow.

Still more alternatively, one or both of the counterweights 100, 102 may comprise differential combination of materials, wherein one side of at least one of the counterweights 100, 102 comprises a more massive or denser material than the other side, which creates eccentricity as defined herein. As those skilled in the art will recognize, creation of eccentricity by differential use of materials within the counterweights 100, 102, e.g., a center of mass offset from the drive shaft's rotational axis, is applicable to any embodiment of the counterweights 100, 102 whether concentric, eccentric, solid burr, partially hollow crown or abrading head or an enlarged section of the drive shaft, or the equivalent.

In one embodiment, the proximal and distal counterweights 100, 102 are substantially equivalent in overall mass as illustrated in FIG. 6, with each counterweight 100, 102 being roughly one half the overall mass of the abrasive section 28, wherein the proximal and distal counterweights 100, 102 are equidistant from the abrasive section 28, wherein the proximal and distal counterweights 100, 102 comprise centers of mass that are equidistant from the axis of rotation of the drive shaft 20 and wherein the proximal and distal counterweights 100, 102 comprise centers of mass are equidistant from the center of mass of the eccentric abrasive section 28. Alternative and equivalent mass distributions between the abrasive section 28 and the counterweight(s) for use in manipulating the orbital rotational diameter of the abrasive section 28 during high-speed rotation will present themselves readily to those skilled in the art and are within the scope of the present invention.

Further, one or both of the counterweights (proximal and/or distal) 100, 102 may be concentric, i.e., spherical or ellipsoidal in profile or other concentric shape, with one or both of the counterweights (proximal and/or distal) 100, 102 having a center of mass that is substantially on, i.e., collinear with, the axis of rotation of the drive shaft 20.

Alternatively, one or both of the counterweights (proximal and/or distal) 100, 102 may be eccentric, i.e., one embodiment may comprise the counterweights (proximal and/or distal) 100, 102 having a center of mass spaced radially from the rotational axis of the drive shaft 20 and aligned within the same longitudinal plane as the center of mass of the eccentric abrasive section 28 as shown in FIG. 6. The radial spacing of the centers of mass of the counterweights may be achieved by spacing the geometric center of each counterweight 100, 102 away from the rotational axis of the drive shaft 20, wherein the proximal counterweight 102 and the distal counterweight 100 each have a center of mass separated from the eccentric abrasive section's 28 center of mass by a rotational angle of 180 degrees as shown in FIG. 6. The centers of mass of the proximal 102 and distal 100 counterweights may be offset 180 degrees. This counterweighting arrangement stimulates orbital motion by the abrasive section 28 and facilitates the ability of the abrasive section 28 to sweep and open the stenotic lesion to a diameter substantially larger than the outer diameter of the resting eccentric enlarged diameter section 28.

An alternative embodiment may comprise at least one of the counterweights 100, 102 having a center of mass that may, or may not be, separated from the abrasive section's 28 center of mass by a rotational angle of 180 degrees. One embodiment of the present invention may dampen the orbital rotational diameter of the abrasive section 28 during high-speed rotation by placing the center of mass of the at least one counterweight 100, 102 at a rotational angle of zero degrees from the center of mass of the abrasive section 28 center of mass. This embodiment may apply whether the abrasive section 28 is eccentric or concentric. For example, dampening may be achieved in an embodiment comprising an eccentric abrasive section 28 by attaching at least one eccentric counterweight 100, 102, wherein the centers of mass of the eccentric abrasive section 28 and the at least one eccentric counterweight 100, 102 are substantially collinear, i.e., with a rotational separation angle of substantially zero degrees. Alternatively, if the abrasive section 28 is provided as a concentric embodiment, with its center of mass on the rotational axis of the drive shaft 20, the at least one counterweight 100, 102 may be provided in a concentric embodiment, with center of mass also located on the rotational axis of the drive shaft 20. More alternatively, if the abrasive section 28 is provided as an eccentric embodiment, with its center of mass located off to rotational axis of drive shaft 20, at least one counterweight may be provided having a center of mass located at a rotational angle of 180 degrees from the center of mass of the abrasive section 28. This embodiment may be provided with the at least one counterweight being on the drive shaft 28 with, or without, a spaced distance between the at least one counterweight and the abrasive section 28.

Those skilled in the art will readily recognize that the respective arrangements of counterweight(s) and abrasive section 28, and centers of mass thereof disclosed herein both infra and supra, may apply to all forms, profiles and types of abrasive section 28 and counterweight(s) discussed herein to either stimulate, i.e., increase the rotational diameter, or dampen, i.e., decrease the rotational diameter, the orbital motion of the abrasive section 28.

Significantly, the present invention may allow use of a smaller diameter abrasive section 28, in conjunction with proximal and distal counterweights 100, 102, while opening a lumen having a swept diameter equivalent to that of larger diameter abrasive sections 28 of the prior art that do not comprise counterweights 100, 102 as described herein.

Those skilled in the art will recognize any number of combinations and permutations of these parameters for a given rotational speed of the drive shaft 20. The skilled artisan will recognize that modification of any of these parameters will either increase or decrease/dampen the diameter of the orbital path taken by the abrasive section. As such, the diameter of the orbital path may be customized for individual lumens.

Another embodiment of the present invention may comprise the abrasive section 28 comprising a concentric enlarged abrasive section of the drive shaft as described in U.S. Pat. No. 5,314,438 to Shturman, the disclosure of which are hereby incorporated by reference in its entirety. Alternatively, the abrasive section 28 of this embodiment may comprise a concentric solid burr attached to the drive shaft as is well known in the art, see e.g., U.S. Pat. No. 4,990,134 to Auth. Concentric in this sense means that the abrasive section 28, either formed of the wire turns or by a solid or semi-solid, i.e., hollow burr comprises a profile that is spherical or ellipsoidal or other concentric shape, with the concentric abrasive section 28 having a center of mass that is substantially on, i.e., collinear with, the axis of rotation of the drive shaft 20.

Further this particular embodiment of the present invention comprises two counterweights 100, 102 attached to or mounted on the drive shaft 20 to stimulate orbital motion of the concentric abrasive section 28. Preferably, a distal counterweight 100 is located distally of the concentric abrasive section 28 and a proximal counterweight 102 is located proximal to the concentric abrasive section 28.

One or both of the proximal and/or distal counterweights 100, 102 may comprise enlarged diameter sections of the drive shaft, formed in similar fashion as the enlarged eccentric diameter abrasive section 28A illustrated in FIG. 6. In this embodiment, the counterweights 100, 102 may be essentially hollow, enlarged wire turns of the drive shaft, formed by use of a mandrel during the wire turn winding process. In the case where only one, either the proximal 102 or the distal 102, counterweight is an enlarged eccentric diameter abrasive section of the drive shaft 20, the remaining counterweight may be either concentric, i.e., center of mass collinear with the drive shaft's axis of rotation and comprising an enlarged diameter section of the drive shaft 20, a solid burr or at least partially hollow abrading head, or may be eccentric and comprising a solid burr or at least partially hollow abrading head.

Alternatively, one or both of the proximal and distal counterweights 100, 102 may be solid and attached to the wire turns of the drive shaft 20 by means well known to those skilled in the art. More alternatively, the proximal and distal counterweights 100, 102 may be at least partially hollow.

In one embodiment wherein the abrasive section 28 is concentric, the proximal and distal counterweights 100, 102 are substantially equivalent in overall mass, with each counterweight 100, 102 being roughly one half the overall mass of the concentric abrasive section 28, wherein the proximal 102 and distal 100 counterweights are equidistant from the concentric abrasive section 100, wherein the proximal and distal centers of mass are equidistant from the axis of rotation of the drive shaft 20 and wherein the proximal and distal centers of mass are equidistant from the center of mass of the concentric abrasive section 28.

The counterweights 100, 102 may be concentric, i.e., spherical or ellipsoidal in profile or other concentric shape, with the counterweights 100, 102 having a center of mass that is substantially on the axis of rotation of the drive shaft 20.

Figure 10:
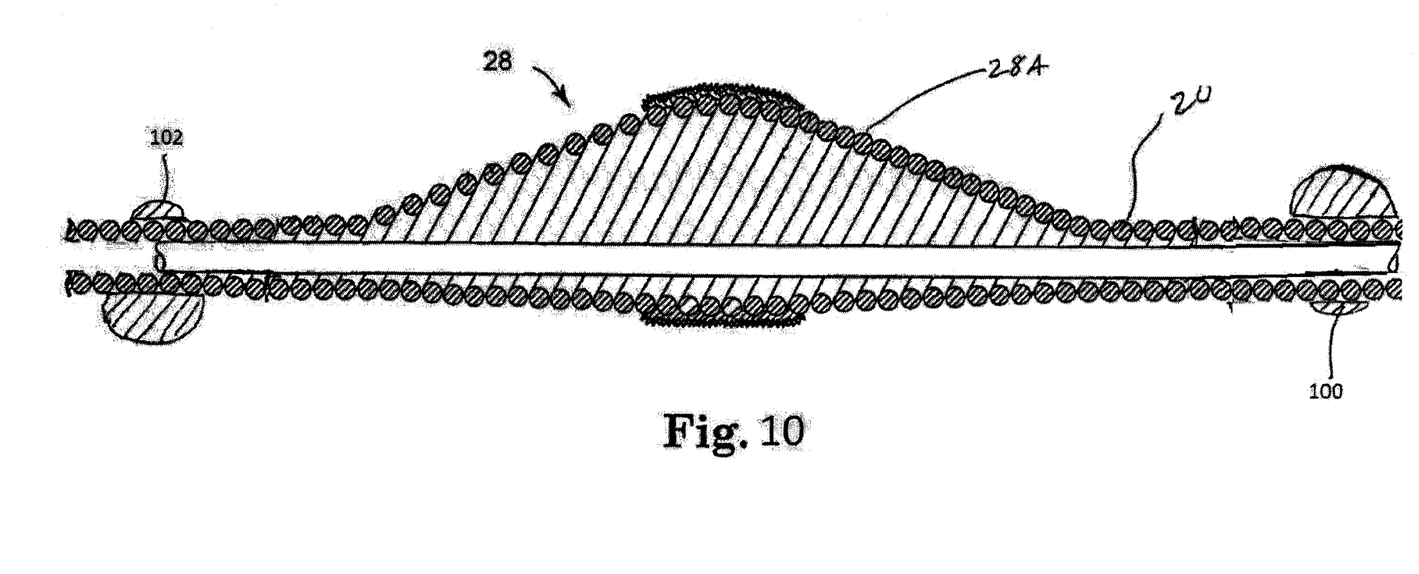
FIG. 10 is a longitudinal cross-section view of one embodiment of the present invention.

Preferably in this embodiment comprising a concentric abrasive section 28, the counterweights 100, 102 are eccentric, i.e., one embodiment may comprise the proximal 102 and distal 100 counterweights having a center of mass spaced radially from the rotational axis of the drive shaft 20, each having the center of mass offset within the same longitudinal plane and within the same longitudinal plane as the center of mass of the concentric abrasive section 28 which is collinear with the axis of rotation. Moreover, the proximal 102 and distal 100 counterweight centers of mass may both be either above the axis of rotation or below the axis of rotation of the drive shaft 20 while both centers of mass are aligned within the same longitudinal plane, creating an "offset" between the center of mass of the abrasive section 28 and the centers of mass of the proximal 102 and distal 100 counterweights. The centers of mass of the proximal 102 and distal 100 counterweights may be offset 180 degrees, or other degree of offset as will be readily recognized by those skilled in the art, from each other around the axis of rotation of the drive shaft 20, as shown in FIG. 10.

As with the eccentric abrasive section embodiment, the concentric abrasive section embodiment may achieve the radial spacing of the centers of mass of the eccentric embodiment of the proximal 102 and distal 100 counterweights by spacing the geometric center of each counterweight 100, 102 away from the rotational axis of the drive shaft 20, wherein the proximal counterweight 102 and the distal counterweight 100 each have a center of mass separated from the concentric abrasive section's center of mass and within the same longitudinal plane. This counterweighting embodiment stimulates orbital motion by the abrasive section 28 and facilitates the ability of the abrasive section 28 to sweep and open the stenotic lesion to a diameter substantially larger than the outer diameter of the resting concentric abrasive section 28. As above, the present invention may allow use of a smaller diameter abrasive section 28, in conjunction with proximal 102 and distal 100 counterweights, while opening a lumen having a swept diameter equivalent to that of larger diameter concentric abrasive sections 28 of the prior art.

Figure 7A:
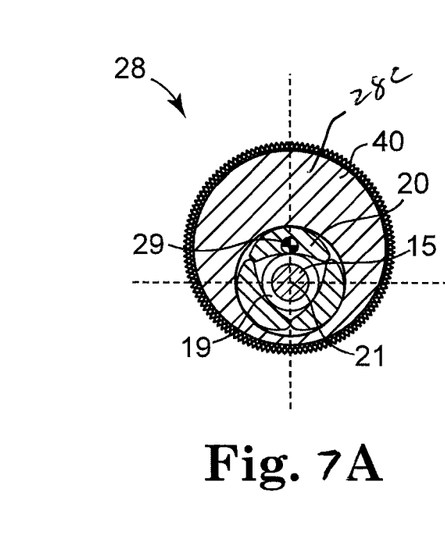
FIG. 7A is a cross-section view of one embodiment of the present invention.
Figure 7B:
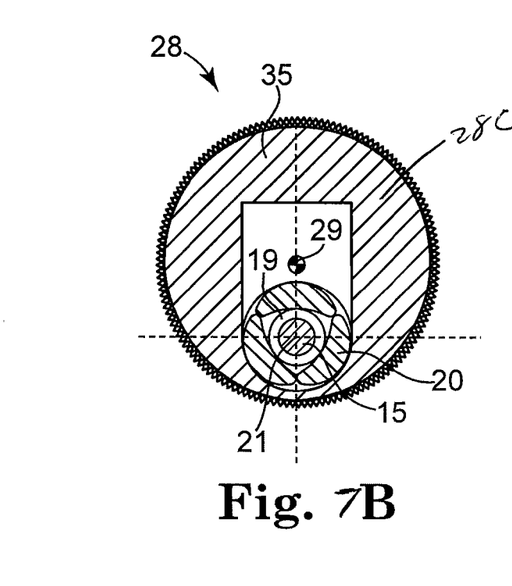
FIG. 7B is a cross-section view of one embodiment of the present invention
Figure 7C:
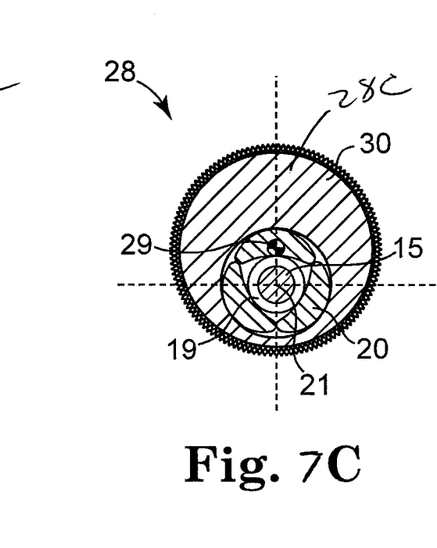
FIG. 7C is a cross-section view of one embodiment of the present invention.

FIGS. 7A-7C depict the positions of the centers of mass 29 of three cross-sectional slices (shown as faces of transverse cross-sections) of the eccentric abrasive section 28, illustrated as an eccentric abrading head 28C as shown in FIGS. 5A, 5B and 5C during high-speed rotation with eccentric counterweights 100, 102 mounted on drive shaft 20 as described herein. The eccentric abrasive section 28 may be divided into many such thin slices, each slice having its own center of mass. FIG. 7B is taken at a position where the abrasive section 28 has its maximum cross-sectional diameter (which, in this case, is the maximum diameter of the intermediate portion 35 of the eccentric abrasive section 28), and FIGS. 7A and 7C are taken, respectively in the distal 40 and proximal 30 portions of the eccentric abrasive section 28. In each of these cross-sectional slices the center of mass 29 is spaced away from the rotational axis of the drive shaft, the rotational axis of the drive shaft 20 coinciding with the center of the guide wire 15. The center of mass 29 of each cross-sectional slice also generally coincides with the geometric center of such cross-sectional slice. FIG. 7B shows the slice having the greatest cross-sectional diameter. In this slice both the center of mass 29 and the geometric center are located the furthest (i.e., maximally spaced away) from the rotational axis of the drive shaft 20. Of course, the center of mass of the entire abrasive section 28 is a composite of the individual centers of mass of multiple slices of the enlarged diameter section, and the overall center of mass will, therefore, be closer to the axis of rotation of the drive shaft 20 than the center of mass of the slice depicted in FIG. 7B.

It should be understood that, as used herein, the word "eccentric" is defined herein to mean either a difference in location between the geometric center of the abrasive section 28 comprising eccentric enlarged diameter section 28A of the drive shaft 20, or an eccentric solid burr 28B, or an eccentric at least partially hollow crown or abrading head 28C, or the eccentric counterweight(s) and the rotational axis of the drive shaft, or to a difference in location between the center of mass of the eccentric abrasive section 28 comprising an eccentric enlarged diameter section 28A, an eccentric solid burr 28B and eccentric and at least partially hollow crown or abrading head 28C, or the eccentric counterweights 100, 102 and the rotational axis of the drive shaft 20. Either such difference, at the proper rotational speeds, will enable the abrasive section 28 to open a stenosis to a diameter substantially greater than the nominal diameter of the abrasive section 28. Moreover, for an eccentric abrasive section 28 having a shape that is not a regular geometric shape, the concept of "geometric center" can be approximated by locating the mid-point of the longest chord which is drawn through the rotational axis of the drive shaft and connects two points on a perimeter of a transverse cross-section taken at a position where the perimeter of the eccentric enlarged diameter section has its maximum length. Moreover, those skilled in the art will recognize that eccentricity as defined may be designed into an abrasive section 28 having a substantially concentric profile, but with one aspect of the profile being more massive than the rest by, e.g., hollowing out a portion of one side of the abrasive section 28.

Moreover, it should also be understood that concentric as used herein, is defined to mean an abrasive section 28 and/or counterweights 100, 102 that comprises a center of mass that is on, i.e., collinear with, the axis of rotation of the drive shaft 20 and a profile that is substantially symmetrical.

Figure 8:
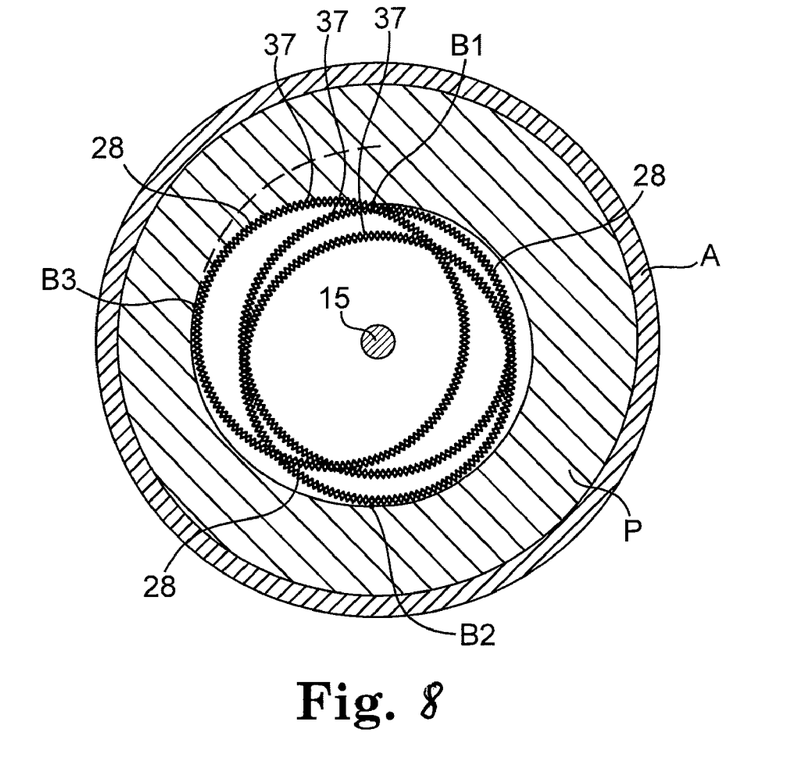
FIG. 8 is a transverse cross-sectional view illustrating three different positions of the rapidly rotating abrasive section of an eccentric rotational atherectomy device of the present invention.
Figure 9:
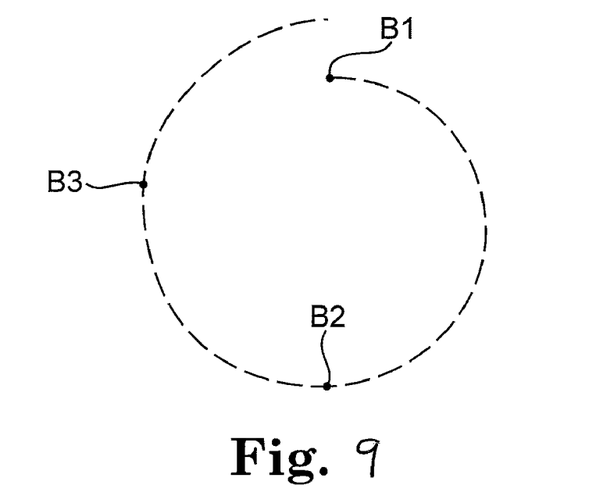
FIG. 9 is a schematic view corresponding to the three positions of the rapidly rotating abrasive section illustrated in FIG. 8.

FIGS. 8 and 9 illustrate the generally spiral orbital path taken by various embodiments of the eccentric abrading head 28 of the present invention, the abrading head 28 shown relative to the guide wire 15 over which the abrading head 28 has been advanced. The pitch of the spiral path in FIGS. 8, 9 is exaggerated for illustrative purposes—in reality, each spiral path of the eccentric enlarged abrading head 28 removes only a very thin layer of tissue via the tissue removing surface 37, and many, many such spiral passes are made by the eccentric enlarged abrading head 28 as the device is repeatedly moved forward and backward across the stenosis to fully open the stenosis. FIG. 9 shows schematically three different rotational positions of the eccentric enlarged abrading head 28 of a rotational atherectomy device of the invention. At each position the abrasive surface of the eccentric enlarged abrading head 28 contacts the plaque "P" to be removed—the three positions are identified by three different points of contact with the plaque "P", those points being designated in the drawing as points B1, B2, and B3. Notice that at each point it is generally the same portion of the abrasive surface of the eccentric enlarged abrading head 28 that contacts the tissue—the portion of the tissue removing surface 37 that is radially most distant from the rotational axis of the drive shaft.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A high-speed rotational atherectomy device for opening a stenosis in an artery having a given diameter, comprising:
   a guide wire having a maximum diameter less than the diameter of the artery;
   a flexible elongated, rotatable drive shaft advanceable over the guide wire, the drive shaft having a rotational axis and an abrasive section, the abrasive section comprising a geometrically concentric profile and further comprising a first side comprising a first material having a density and a second side comprising a second material having a density higher than that of the density of the first material, and a center of mass, the center of mass spaced radially from the rotational axis of the drive shaft into the second side of the drive shaft in a longitudinal plane as a result of the densities of the first and second materials;

a proximal counterweight on the drive shaft on the proximal side of the abrasive section, the proximal counterweight comprising a geometrically concentric profile and a first side comprising a first material having a density and a second side comprising a second material having a density higher than that of the density of the first material, and a center of mass, the center of mass spaced radially from the rotational axis of the drive shaft into the second side of the proximal counterweight as a result of the densities of the first and second materials, the center of mass of the proximal counterweight spaced radially from the rotational axis of the drive shaft in the same longitudinal plane as the center of mass of the abrasive element;

and a distal counterweight on the drive shaft on the distal side of the abrasive section, the distal counterweight comprising a geometrically concentric profile and a first side comprising a first material having a density and a second side comprising a second material having a density higher than that of the density of the first material, and a center of mass, the center of mass spaced radially from the rotational axis of the drive shaft into the second side of the distal counterweight as a result of the densities of the first and second materials, the center of mass of the distal counterweight spaced radially from the rotational axis of the drive shaft in the same longitudinal plane as the center of mass of the abrasive element wherein the center of mass of the proximal counterweight is radially offset from the center of mass of the distal counterweight at a rotational angle of 180 degrees, wherein the center of mass of only one of the proximal counterweight and the distal counterweight is radially offset at a rotational angle of 180 degrees from the center of mass of the abrasive element in the longitudinal plane.

2. The high-speed rotational atherectomy device of claim 1, further comprising the radial spacing center of mass of the proximal counterweight comprising a first distance from the center of mass to the rotational axis of the drive shaft, and the radial spacing of the distal counterweight from the rotational axis of the drive shaft comprising a second distance from the center of mass to the rotational axis of the drive shaft, the first and second distances being equivalent.

3. A high-speed rotational atherectomy device for opening a stenosis in an artery having a given diameter, comprising:
a guide wire having a maximum diameter less than the diameter of the artery;
a flexible elongated, rotatable drive shaft advanceable over the guide wire, the drive shaft having a rotational axis and an abrasive section, the abrasive section comprising a geometrically concentric profile and further comprising a first side comprising a first material having a density and a second side comprising a second material having a density higher than that of the density of the first material, and a center of mass, the center of mass spaced radially from the rotational axis of the drive shaft into the second side of the drive shaft in a longitudinal plane as a result of the densities of the first and second materials;
a proximal counterweight on the drive shaft on the proximal side of the abrasive section, the proximal counterweight comprising a geometrically eccentric profile and a center of mass spaced radially from the rotational axis of the drive shaft as a result of the geometric eccentric profile, the center of mass of the proximal counterweight spaced radially from the rotational axis of the drive shaft in the same longitudinal plane as the center of mass of the abrasive element;

and a distal counterweight on the drive shaft on the distal side of the abrasive section, the distal counterweight comprising a geometrically eccentric profile and a center of mass spaced radially from the rotational axis of the drive shaft as a result of the geometric eccentric profile, the center of mass of the distal counterweight spaced radially from the rotational axis of the drive shaft in the same longitudinal plane as the center of mass of the abrasive element, wherein the center of mass of the proximal counterweight is radially offset from the center of mass of the distal counterweight at a rotational angle of 180 degrees, wherein the center of mass of only one of the proximal counterweight and the distal counterweight is radially offset at a rotational angle of 180 degrees from the center of mass of the abrasive element in the longitudinal plane.

4. The high-speed rotational atherectomy device of claim 3, further comprising the radial spacing center of mass of the proximal counterweight comprising a first distance from the center of mass to the rotational axis of the drive shaft, and the radial spacing of the distal counterweight from the rotational axis of the drive shaft comprising a second distance from the center of mass to the rotational axis of the drive shaft, the first and second distances being equivalent.

5. A high-speed rotational atherectomy device for opening a stenosis in an artery having a given diameter, comprising:
a guide wire having a maximum diameter less than the diameter of the artery;
a flexible elongated, rotatable drive shaft advanceable over the guide wire, the drive shaft having a rotational axis and an abrasive section, the abrasive section comprising a geometrically eccentric profile the center of mass spaced radially from the rotational axis of the drive shaft in a longitudinal plane as a result of the geometrically eccentric profile;
a proximal counterweight on the drive shaft on the proximal side of the abrasive section, the proximal counterweight comprising a geometrically concentric profile and a first side comprising a first material having a density and a second side comprising a second material having a density higher than that of the density of the first material, and a center of mass, the center of mass spaced radially from the rotational axis of the drive shaft into the second side of the proximal counterweight as a result of the densities of the first and second materials, the center of mass of the proximal counterweight spaced radially from the rotational axis of the drive shaft in the same longitudinal plane as the center of mass of the abrasive element, and a distal counterweight on the drive shaft on the distal side of the abrasive section, the distal counterweight comprising a geometrically concentric profile and a first side comprising a first material having a density and a second side comprising a second material having a density higher than that of the density of the first material, and a center of mass, the center of mass spaced radially from the rotational axis of the drive shaft into the second side of the distal counterweight as a result of the densities of the first and second materials, the center of mass of the distal counterweight spaced radially from the rotational axis of the drive shaft in the same longitudinal plane as the center of mass of the abrasive element wherein the center of mass of the proximal counterweight is radially offset from the center of mass of the distal counterweight at a rotational angle of 180 degrees, wherein the center of mass of only one of the proximal counterweight and the distal counterweight is radially offset at a rotational angle of 180 degrees from the center of mass of the abrasive element in the longitudinal plane.

6. The high-speed rotational atherectomy device of claim 5, further comprising the radial spacing center of mass of the proximal counterweight comprising a first distance from the center of mass to the rotational axis of the drive shaft, and the radial spacing of the distal counterweight from the rotational axis of the drive shaft comprising a second distance from the center of mass to the rotational axis of the drive shaft, the first and second distances being equivalent.

* * * * *